(12) United States Patent
Deeley et al.

(10) Patent No.: US 11,377,615 B2
(45) Date of Patent: Jul. 5, 2022

(54) SELECTIVE ACETALIZATION / ETHERIFICATION PROCESS

(71) Applicant: BP P.L.C., London (GB)

(72) Inventors: Jon Deeley, London (GB); Gareth Armitage, London (GB); Fiona Jackson, London (GB)

(73) Assignee: BP P.L.C., London (GB)

( * ) Notice: Subject to any disclaimer, the term of this patent is extended or adjusted under 35 U.S.C. 154(b) by 124 days.

(21) Appl. No.: 16/757,415

(22) PCT Filed: Oct. 19, 2018

(86) PCT No.: PCT/EP2018/078802
§ 371 (c)(1),
(2) Date: Apr. 19, 2020

(87) PCT Pub. No.: WO2019/077147
PCT Pub. Date: Apr. 25, 2019

(65) Prior Publication Data
US 2021/0363454 A1    Nov. 25, 2021

(30) Foreign Application Priority Data
Oct. 19, 2017   (GB) .................................... 1717210

(51) Int. Cl.
*C10M 129/16* (2006.01)
*C07C 41/28* (2006.01)
*C07C 41/48* (2006.01)
*C10M 169/04* (2006.01)
*C10N 40/25* (2006.01)

(52) U.S. Cl.
CPC .......... *C10M 129/16* (2013.01); *C07C 41/28* (2013.01); *C07C 41/48* (2013.01); *C10M 169/04* (2013.01); *C10M 2203/003* (2013.01); *C10M 2207/04* (2013.01); *C10N 2040/25* (2013.01)

(58) Field of Classification Search
CPC .............. C10M 129/16; C10M 169/04; C10M 2203/003; C10M 2207/04; C07C 41/28; C07C 41/48; C10N 2040/25
See application file for complete search history.

(56) References Cited

U.S. PATENT DOCUMENTS

| | | | |
|---|---|---|---|
| 3,102,150 A | 8/1963 | Hunter et al. | |
| 4,088,700 A * | 5/1978 | Watts, Jr. ............... | C07C 41/28 568/671 |
| 4,413,149 A * | 11/1983 | Fischer .................... | C07C 41/28 568/636 |
| 4,479,017 A | 10/1984 | Ayusawa et al. | |
| 5,399,631 A * | 3/1995 | Egawa ..................... | C07C 43/15 525/328.9 |
| 5,523,491 A | 6/1996 | Egawa et al. | |
| 5,589,597 A | 12/1996 | Egawa et al. | |
| 6,087,539 A | 7/2000 | Yamasaki et al. | |
| 6,313,322 B1 | 11/2001 | Hieber et al. | |
| 7,622,431 B2 | 11/2009 | Muir | |
| 2005/0198894 A1 | 9/2005 | Migdal et al. | |
| 2006/0090393 A1 | 5/2006 | Rowland et al. | |
| 2013/0109604 A1 | 5/2013 | Patil et al. | |

FOREIGN PATENT DOCUMENTS

| | | |
|---|---|---|
| EP | 1533362 A1 | 11/2004 |
| GB | 1581412 A | 12/1980 |
| WO | 95/01949 A1 | 1/1995 |
| WO | 1999/021902 A1 | 5/1999 |
| WO | 2003/099890 A3 | 12/2003 |
| WO | 2004/046073 A1 | 6/2004 |
| WO | 2006/099250 A1 | 9/2006 |
| WO | 2014/096096 A1 | 6/2014 |

OTHER PUBLICATIONS

International Search Report for PCT/EP2018/078801, 3 pages, dated Jan. 18, 2019.
International Search Report for PCT/E{2018/078802, 4 pages, dated Jan. 28, 2019.
Bakos et al., "Auto-Tandem Catalysis with Frustrated Lewis Pairs for Reductive Etherification of Aldehydes and Ketones" Angew. Chem. Int. Ed. 56: 5217-5221 (2017).
Smith et al., "Role of Acetal Formation in Metal Catalyzed Hydrogenation and Exchange of Cinnamaldehyde" Catalysis in Organic Synthesis, p. 33-65 (1977).
Eliel et al., "Reduction of Acetals to Ethers by Means of Lithium Aluminum Hydride-Aluminum Chloride" J. Org. Chem. 23: 1088(1958).
Ohta et al., "Reductive cleavage of the C—O bond of acetals and orthoesters: reduction by silane in the presence of a Rh-PPh3 complex" Chem. Commun. 1192-1193 (2003).
Tsunoda et al., "Reaction of acetals and trialkylsilanes catalyzed by trimethylsilyl liinuoromethanesulfonate. A simple method for conversion of acetals to ethers" Tetrahedron Lett. 48: 4679-4680 (1979).
Post, "The Reaction of Certain Orthoesters with Aldehydes" Orthoesters and Aldehydes, 244-249 (1939).
Kotke et al., "Acid-free, organocatalytic acetalization" Tetrahedron, 62:434-439 (2006).
McElvain et al., "Ketene Acetals. XXIII. Dealcoholation of Orthoesters with Aluminum t-Butoxide" J. Am. Chem. Soc. 73: 1400-1402(1951).
Claus et al. "A New Method of Conversion of Nitriles to Aldehydes 1" J. Am. Chem. Soc. 73(10): 5005-5006 (1951).

(Continued)

*Primary Examiner* — Ellen M McAvoy
(74) *Attorney, Agent, or Firm* — McDonnell Boehnen Hulbert & Berghoff LLP

(57) ABSTRACT

The present invention relates to a selective process for preparing acetals or ethers. In particular, the process involves a selective catalytic hydrogenolysis of a trihydrocarbyl orthoestersо as to control the extent of dealcoholation to afford either the corresponding acetal or ether product. Ether products preparable by means of the present invention include ethers which are suitable for use as base stocks in lubricating compositions.

21 Claims, No Drawings

(56) References Cited

OTHER PUBLICATIONS

Staudinger et al., "Ketene: Uber Ketenacetale" Helvetica Chimica Acti 5(5): 645-655 (1922).
Sigmund et al., "Uber die katalytische Spaltung von Orthoestern an Aluminumoxyd" Monatshefte Fur Chemie 58(1): 280-288 (1931).
Search Report for GB1717211.5, 2 pages, dated Aug. 1, 2018.
Search Report for GB 1717210.7, 2 pages, dated Aug. 1, 2018.
Bhattacharjee et al., "Hydrogenolysis of carbohydrate acetals, ketals, and cyclic orthoesters with lithium aluminum hydride—aluminum trichloride" Canadian J. Chem. 47(7):1195-1206 (1969).

\* cited by examiner

SELECTIVE ACETALIZATION / ETHERIFICATION PROCESS

This application is a national stage application under 35 U.S.C. § 371 of International Application No. PCT/EP2018/078802, filed Oct. 19, 2018, which claims priority to Great Britain Application No. GB 1717210.7, filed Oct. 19, 2017, the disclosures of which are explicitly incorporated by reference herein.

The present invention relates to a selective process for preparing acetals or ethers. In particular, the process involves a selective catalytic hydrogenolysis of a trihydrocarbyl orthoester so as to control the extent of dealcoholation to afford either the corresponding acetal or ether product. Ether products preparable by means of the present invention include ethers which are suitable for use as base stocks in lubricating compositions.

BACKGROUND

Ether compounds are an important category of compounds which have found application in a variety of industries as functional additives (for instance, cosmetic, fuel or lubricant additives), solvents, diluents and as important precursors for other industrial and/or commercially desirable compounds. Acetals are most commonly associated with protecting group chemistry and typically find application as protected precursors and intermediates for ether compounds in an industrial setting. Acetals do however have several additional applications in their own right, including use as acetal resins.

Known processes for preparing ethers on an industrial scale include the reaction of an alcohol with an alkyl group having a suitable leaving group, such as a halogen (for example bromine, chlorine or iodine) or a sulfonate ester (for example mesylate or tosylate), in the presence of a base (for example potassium hydroxide or potassium tert-butoxide) and a catalyst (for example Starks' catalyst: N-Methyl-N,N,N-trioctyloctan-1-ammonium chloride). However, such processes have the disadvantage of generating corrosive halogenated or sulfonate ester intermediates.

An alternative approach to etherification which avoids the formation of these undesirable intermediates is the reaction of an alcohol with an alkene. A well-known example of such an etherification relates to the preparation of methyl or ethyl tert-butyl ether (MTBE or ETBE), which are well known fuel additives. This same approach has also been utilized more recently in the preparation of ether compounds for use in improving one or more of solubility and dispersancy of lubricating compositions, as illustrated in US 2013/0109604 (Example 3 thereof).

Another approach to the formation of ethers which avoids the formation of corrosive by-products is through conversion of acetals to the corresponding ether by hydrogenolysis. Typically, this involves subjecting the acetal compound to hydrogen under conditions of elevated temperature and pressure in the presence of a suitable hydrogenation catalyst.

U.S. Pat. No. 5,523,491 describes the conversion of an acetal or ketal compound to the ether by means of hydrogenation in the presence of solid acidic catalyst having hydrogenating ability or a solid acid catalyst in combination with a hydrogenation catalyst. The process of the disclosure is said to be particularly suitable for forming polyvinyl ether compounds suitable for use in a lubricating oil for compression-type refrigerators. This document provides no indication of how the acetal/ketal starting materials may be formed.

U.S. Pat. No. 4,479,017 describes a catalytic hydrogenolysis of an acetal compound of formula (2) with a palladium catalyst on a carbon carrier to produce an ether compound. The acetal compound of formula (2) is said to be suitably derived from the standard reaction of an alcohol and a carbonyl compound (column 2, lines 38 to 47).

U.S. Pat. No. 6,087,539 describes the formation of a vinyl ether polymer compound of formula (II) or (III) from the reaction of a vinyl ether polymer of formula (I) having a terminal acetal group with hydrogen in the presence of a solid catalyst comprising nickel and an oxide of silicon, aluminium, magnesium, titanium, zirconium and combinations thereof. The starting material is said to be preparable from polymerization of an alkyl vinyl ether in the presence of an acetal compound and other conventional methods.

WO 95/01949 describes the conversion of acetals to ethers, in particular 3-alkoxypropiaonaldehyde dialkyl acetal to the corresponding 1,3-dialkoxypropane, in the presence of a supported hydrogenation catalyst comprising at least one catalytic metal selected from Pd, Ni, Co, Pt, Rh and Ru, and a supported material selected from silica, alumina silica-alumina, alumino-silicates and carbon.

Alternative methods for converting an acetal to the corresponding ether includes reduction with lithium aluminium hydride-aluminium chloride, as reported for instance in Eliel et al., Communications, vol. 23, 1958, page 1088. Other methods of forming ethers from acetals include reductive cleavage of the C—O bond of the acetal with silane, as described in Chem. Commun., 2003, 1192-1193, and in Tetrahedron Letters, vol. 20, Issue 48, 1979, pages 4679-4680.

Where details of how the acetal compound employed in the above disclosures is itself prepared are provided, conventional methods are said to be relied upon, such as the reaction of an alcohol and a suitable aldehyde. This reaction is thermodynamically unfavourable and therefore typically requires the presence of an acidic catalyst.

An alternative method for forming an acetal compound is by reaction of an aldehyde and an orthoester. Post H. W., "*The Reaction of Certain Orthoesters with Aldehydes*", Orthoesters and aldehydes, 1939, pages 244 to 249, describes the reaction of an alkyl orthoformate with acetaldehyde, catalyzed by concentrated sulfuric acid, to produce the corresponding acetal. More recently, Schreiner et al., "*Acid free, organocatalytic acetalization*", Tetrahedron, 63, 2006, pages 434 to 439, reviews the use of different catalysts for acetalization reactions and proposes an alternative non-acidic catalyst in the form of an electron deficient thiourea derivative which may be used for acetalization of an aldehyde with an alkyl orthoester.

McElvain, S. M. et al., J. Am. Chem. Soc., 1951, 73(4), pages 1400-1402, describes a process for producing ketene acetals from orthoesters through dealcoholation with aluminum t-butoxide. Only partial dealcoholation is said to occur with the lower boiling and less reactive aliphatic orthoesters such as methyl orthopropionate and methyl orthoisobutyrate.

It has been found by the inventors that trihydrocarbyl orthoesters can be employed as useful starting materials in a process for selectively preparing an acetal or an ether product as desired. In particular, the present invention is based on the surprising discovery that trihydrocarbyl orthoesters may undergo catalytic hydrogenolysis and that the operation temperatures may be selected in order to conveniently direct the product distribution towards the synthesis of the product acetal or ether, as desired.

SUMMARY

Accordingly, in a first aspect, an acetalization process is provided, said process comprising the step of:
i) subjecting a trihydrocarbyl orthoester to hydrogenolysis in the presence of a hydrogenation catalyst to form an acetal;
wherein hydrogenolysis is performed at a temperature of 125° C. or less.

In preferred embodiments, the hydrogenolysis step of the acetlization is performed at a temperature of 15° C. to 120° C., more preferably from 20° C. to 110° C., yet more preferably from 40° C. to 105° C., most preferably from 60° C. to 100° C.

In a second aspect, the present invention provides an etherification process, said process comprising the step of:
i) subjecting a trihydrocarbyl orthoester to hydrogenolysis in the presence of a hydrogenation catalyst to form an ether;
wherein hydrogenolysis is performed at a temperature of 140° C. or greater.

In preferred embodiments, the hydrogenolysis step of the etherification is performed at a temperature from 140° C. to 350° C., more preferably from 150° C. to 300° C., yet more preferably from 160° C. to 270° C., most preferably from 175° C. to 250° C.

In other preferred embodiments, the trihydrocarbyl orthoester starting material utilized in the processes of the present invention is of formula (I):

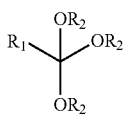

(I)

wherein: $R_1$ is selected from H and aliphatic hydrocarbyl; and $R_2$ is aliphatic hydrocarbyl.

Also provided are processes which, following preparation of the ether compound, include formulation of a lubricating composition comprising the ether compound and use of the resulting lubricant composition for lubricating a surface.

DETAILED DESCRIPTION

An acetalization process is provided, said process comprising the step of:
i) subjecting a trihydrocarbyl orthoester to hydrogenolysis in the presence of a hydrogenation catalyst to form an acetal;
wherein hydrogenolysis is performed at a temperature of 125° C. or less.

In addition, an etherification process is provided, said process comprising the step of:
i) subjecting a trihydrocarbyl orthoester to hydrogenolysis in the presence of a hydrogenation catalyst to form an ether;
wherein hydrogenolysis is performed at a temperature of 140° C. or greater.

For the purposes of the present invention, the following terms as used herein shall, unless otherwise indicated, be understood to have the following meanings:

The term "hydrocarbyl" as used herein in connection with the trihydrocarbyl orthoester reactant employed in the process of the invention, refers to a group comprising hydrogen and carbon atoms, where one or more carbon atoms may optionally be replaced with —O—, which group may be saturated or unsaturated, preferably saturated, and contains up to 40 carbon atoms. Examples of hydrocarbyl groups include hydrocarbyl groups containing from 4 to 28 carbon atoms, such as from 6 to 26 carbon atoms or from 8 to 24 carbon atoms. Where one or more of the carbon atoms is replaced with —O—, from 2% to 35% of the carbon atoms are preferably replaced with —O—, or from 5% to 25%. In other examples, the hydrocarbyl group has 1 to 3 carbon atoms replaced with —O—, for example 2 carbon atoms replaced with —O—. In other examples, none of the carbon atoms are replaced with —O—. The hydrocarbyl group may be aromatic or aliphatic, or comprise both aromatic and aliphatic portions. Preferably, the hydrocarbyl group is aliphatic, or at least comprises an aliphatic portion.

Examples of hydrocarbyl groups include acyclic groups, non-aromatic cyclic groups, aromatic groups and groups comprising both an acyclic portion and a non-aromatic cyclic/aromatic portion. The hydrocarbyl group may be a straight-chained or branched-chained group. The hydrocarbyl group includes monovalent groups and polyvalent groups as specified. Examples of monovalent hydrocarbyl groups include alkyl, alkenyl, alkynyl, carbocyclyl (e.g. cycloalkyl, cycloalkenyl or aryl) and aralkyl.

The term "alkyl" as used herein refers to a monovalent straight- or branched-chain alkyl moiety containing from 1 to 40 carbon atoms. Examples of alkyl groups include alkyl groups containing from 1 to 30 carbon atoms, e.g. from 1 to 20 carbon atoms, e.g. from 1 to 14 carbon atoms. Particular examples include alkyl groups containing 1, 2, 3, 4, 5 or 6 carbon atoms. Examples of alkyl groups include methyl, ethyl, n-propyl, isopropyl, n-butyl, sec-butyl, tert-butyl, pentyl, hexyl and the like. Unless specifically indicated otherwise, the term "alkyl" does not include optional substituents.

The term "cycloalkyl" as used herein refers to a monovalent saturated aliphatic hydrocarbyl moiety containing from 3 to 40 carbon atoms and containing at least one ring, wherein said ring has at least 3 ring carbon atoms. The cycloalkyl groups mentioned herein may optionally have alkyl groups attached thereto. Examples of cycloalkyl groups include cycloalkyl groups containing from 3 to 16 carbon atoms, e.g. from 3 to 10 carbon atoms. Particular examples include cycloalkyl groups containing 3, 4, 5 or 6 ring carbon atoms. Examples of cycloalkyl groups include groups that are monocyclic, polycyclic (e.g. bicyclic) or bridged ring system. Examples of cycloalkyl groups include cyclopropyl, cyclobutyl, cyclopentyl, cyclohexyl and the like. "Cycloalkenyl" groups correspond to non-aromatic cycloalkyl groups containing at least one carbon-carbon double bond.

The term "alkenyl" as used herein refers to a monovalent straight- or branched-chain alkyl group containing from 2 to 40 carbon atoms and containing, in addition, at least one carbon-carbon double bond, of either E or Z configuration unless specified. Examples of alkenyl groups include alkenyl groups containing from 2 to 20 carbon atoms, e.g. from 2 to 12 carbon atoms, e.g. from 2 to 10 carbon atoms. Particular examples include alkenyl groups containing 2, 3, 4, 5 or 6 carbon atoms. Examples of alkenyl groups include ethenyl, 2-propenyl, 1-butenyl, 2-butenyl, 3-butenyl, 1-pentenyl, 2-pentenyl, 3-pentenyl, 1-hexenyl, 2-hexenyl, 3-hexenyl and the like.

The term "aryl" as used herein refers to an aromatic carbocyclic ring system containing from 6 to 14 ring carbon atoms. Examples of aryl groups include aryl groups containing from 6 to 10 ring carbon atoms, e.g. 6 ring carbon atoms. An example of an aryl group includes a group that is a monocyclic aromatic ring system or a polycyclic ring system containing two or more rings, at least one of which is aromatic. Examples of aryl groups include aryl groups that comprise from 1 to 6 exocyclic carbon atoms in addition to ring carbon atoms. Examples of aryl groups include aryl groups that are monovalent or polyvalent as appropriate. Examples of monovalent aryl groups include phenyl, benzyl naphthyl, fluorenyl, azulenyl, indenyl, anthryl and the like. An example of a divalent aryl group is 1,4-phenylene.

The term "alkylene" as used herein refers to a divalent straight- or branched-chain saturated hydrocarbyl group consisting of hydrogen and carbon atoms and containing from 1 to 30 carbon atoms. Examples of alkylene groups include alkylene groups that contain from 1 to 20 carbon atoms, e.g. from 1 to 12 carbon atoms, e.g. from 1 to 10 carbon atoms. Particular examples include alkylene groups that contain 1, 2, 3, 4, 5 or 6 carbon atoms.

The term "cycloalkyl-substituted-alkyl" as used herein refers to a straight- or branched-chain alkyl group in which one of the hydrogens of the alkyl chain is replaced with a cycloalkyl group as described hereinabove.

In particularly preferred embodiments, $R_1$ is selected from H, $C_1$-$C_{18}$ alkyl, $C_3$-$C_{18}$ cycloalkyl and $C_4$-$C_{18}$ cycloalkyl-substituted-alkyl and $R_2$ is $C_1$-$C_{18}$ alkyl, $C_3$-$C_{18}$ cycloalkyl and $C_4$-$C_{18}$ cycloalkyl-substituted-alkyl.

In some embodiments, the trihydrocarbyl orthoester starting material utilized in the processes of the present invention is of formula (I):

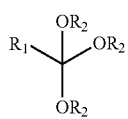

(I)

wherein: $R_1$ is selected from H and aliphatic hydrocarbyl; and $R_2$ is aliphatic hydrocarbyl.

In preferred embodiments, $R_1$ is selected from H, $C_1$-$C_{40}$ alkyl, $C_3$-$C_{40}$ cycloalkyl and $C_4$-$C_{40}$ cycloalkyl-substituted-alkyl and $R_2$ is selected from $C_1$-$C_{40}$ alkyl, $C_3$-$C_{40}$ cycloalkyl and $C_4$-$C_{40}$ cycloalkyl-substituted-alkyl. More preferably, $R_1$ is selected from H, $C_1$-$C_{20}$ alkyl, $C_5$-$C_{30}$ cycloalkyl and $C_7$-$C_{30}$ cycloalkyl-substituted-alkyl and $R_2$ is selected from $C_1$-$C_{20}$ alkyl, $C_5$-$C_{30}$ cycloalkyl and $C_7$-$C_{30}$ cycloalkyl-substituted-alkyl.

Preferred examples of the trihydrocarbyl orthoesters include 1,1,1-triethoxypropane.

The trihydrocarbyl orthoester utilized in accordance with the present invention may be obtained commercially or prepared by any suitable means known in the art. A preferred method for preparing a desired trihydrocarbyl orthoester involves transesterifying trimethyl orthoformate/triethyl orthoformate with an alcohol, for instance having a long-chained hydrocarbyl portion, in the presence of an acidic catalyst. This approach has been found to be a reliable and convenient means for generating more complex orthoesters which may subsequently be used in the acetalization/etherification reactions of the invention in order to form more complex products.

Thus, in some embodiments, the process of the invention, further comprises the preceding step of preparing a trihydrocarbyl orthoester of formula (I) where $R_2$ is $C_4$-Cao alkyl, $C_3$-$C_{40}$ cycloalkyl and $C_4$-$C_{40}$ cycloalkyl-substituted-alkyl, said preceding step comprising reacting a trimethyl orthoester and/or triethyl orthoester with a molar excess of an alcohol of formula $R_2OH$ in the presence of an acidic catalyst, where $R_2$ is $C_4$-$C_{40}$ alkyl, $C_3$-$C_{40}$ cycloalkyl and $C_4$-$C_{40}$ cycloalkyl-substituted-alkyl.

Examples of acid catalysts that may be used for the transesterification reaction include p-toluenesulfonic acid, benzenesulfonic acid, methanesulfonic acid, sulfuric acid, hydrochloric acid, phosphoric acid and an acidic ion-exchange resin. Most preferably the acid catalyst which is employed is p-toluenesulfonic acid.

Examples of suitable acidic ion-exchange resins include acidic macroreticular-type ion-exchange resin or an acidic gel-type ion-exchange resin. Typically, the acidic gel-type cation exchange resins that may be used are based on an insoluble cross-linked polymeric matrix, typically having a pore diameter of at most 30 Å. In preferred embodiments, the acidic gel-type cation exchange resins are based on a cross-linked polystyrene based matrix, preferably having a pore diameter of at most 30 Å. More preferably, the acidic gel-type cation exchange resins that may be used are based on a cross-linked polymeric matrix prepared by copolymerising styrene and divinyl benzene and preferably having a pore diameter of at most 30 Å.

In preferred embodiments, the acidic gel-type cation exchange resins are strong acid ion exchange resins, such as sulfonated resins. In particular, the acidic gel-type cation exchange resins are preferably based on a sulfonated insoluble cross-linked polymeric matrix preferably having a pore diameter of at most 30 Å. In a particularly preferred embodiment, the acidic gel-type cation exchange resin used is based on a sulfonated copolymer of styrene and divinyl benzene, preferably having a pore diameter of at most 30 Å.

Examples of suitable acidic gel-type cation exchange resins include, but are not limited to, the strong acid Dowex (trademark) gel-type ion exchange resins, the strong acid Amberlyst (trademark) gel-type ion exchange resins, the strong acid Diaion (trademark) gel-type ion exchange resins, the strong acid Lewatit (trademark) gel-type ion exchange resins, the strong acid Purolite (trademark) gel-type ion exchange resins, the strong acid gel-type ion exchange resins available from ResinTech Inc., and mixtures thereof.

The acidic macroreticular-type cation exchange resins useful in the present invention are typically based on an insoluble cross-linked polymeric matrix typically having a pore diameter in the range of from 50 to 1,000,000 Å. In preferred embodiments, the acidic macroreticular-type cation exchange resins used in the process of the present invention are based on a cross-linked polystyrene based matrix having a pore diameter in the range of from 50 to 1,000,000 Å. More preferably, the acidic macroreticular-type cation exchange resins useful in the process of the present invention are based on a cross-linked polymeric matrix prepared by copolymerising styrene and divinyl benzene, having a pore diameter in the range of from 50 to 1,000,000 Å.

In preferred embodiments, the acidic macroreticular-type cation exchange resins used in the process of the present invention are strong acid ion exchange resins, such as sulfonated resins. In particular, the acidic macroreticular-type cation exchange resins used in the process of the present invention are preferably based on a sulfonated insoluble cross-linked polymeric matrix preferably having a pore diameter in the range of from 50 to 1,000,000 Å. Thus, in a particularly preferred embodiment, the acidic macroreticular-type cation exchange resins used in the process of the present invention are sulfonated copolymers of styrene and divinyl benzene, having a pore diameter in the range of from 50 to 1,000,000 Å.

Suitable acidic macroreticular-type cation exchange resins include, but are not limited to, the strong acid Dowex macroreticular-type ion exchange resins, the strong acid Amberlyst macroreticular-type ion exchange resins, the strong acid Diaion macroreticular-type ion exchange resins, the strong acid Lewatit macroreticular-type ion exchange resins, the strong acid Purolite macroreticular-type ion exchange resins, the strong acid macroreticular-type ion exchange resins available from ResinTech Inc., and mixtures thereof.

In further regard to the transesterification, the trimethyl orthoester and/or triethyl orthoester and alcohol of formula $R_2OH$ are preferably contacted in a molar ratio of at least 5:1, preferably at least 8:1, more preferably at least 10:1. These reactants may be contacted by any suitable means of which the skilled person is familiar. For instance, the reactants may be contacted within a reactor and may be fed into the reactor either separately or pre-mixed. Where an acidic ion-exchange resin is employed as an acidic catalyst, the reactants may initially all contact the solid catalyst at the same portion of the solid catalyst, or they may be added at different positions of the solid catalyst. The initial point of contact of the reactants with the solid catalyst is the point at which the reactants initially contact each other in the presence of the solid catalyst. The reactants may flow co-currently or counter-currently over the solid catalyst.

The transesterification step may be carried out in any suitable heterogeneous or homogeneous catalytic reactor, in particular the known types of liquid-phase reactors (including but not limited to plug flow, continuously stirred tank, loop reactors or combinations thereof). Reactive separations, such as catalytic distillation, can also be employed in accordance with the present invention, which may be useful in a continuous process where production and removal of products occurs simultaneously. The reactants may be in a gaseous phase and/or a liquid phase. The reaction can be carried out in a continuous, semi-continuous or a batch-type mode.

The trimethyl orthoester and/or triethyl orthoester and the alcohol of formula $R_2OH$ are contacted at a temperature which is suitable for achieving conversion of a major portion of the orthoester reactant and which avoids decomposition of the reactants and does not, for instance, exceed the temperature limit at which any solid acidic catalyst which is present remains stable. In particular, where an acidic ion-exchange resin is employed in connection with the invention, high temperatures can lead to resin decomposition and leaching which is undesirable. A suitable range of temperatures for use in connection with the transesterification reaction where an acidic ion-exchange resin catalyst is employed of the present invention is from 30° C. to 120° C. In preferred embodiments, the reactants are contacted at a temperature of from 50° C. to 100° C., more preferably from 70° C. to 90° C., for example 80° C., when an acidic ion-exchange resin catalyst is employed. Higher temperatures may be used where alternative acidic catalysts are used, such as those described hereinbefore. For example, the reaction may be conducted over temperatures from 50° C. to 150° C., preferably from 70° C. to 140° C., more preferably from 80° C. to 120° C.

The transesterification reaction may be performed over a range of pressures. A suitable range of pressures for use in connection with the present invention is from 50 kPa to 5,000 kPa. In preferred embodiments, the reactants are contacted at a pressure from 100 kPa to 1,000 kPa, more preferably from, 100 kPa to 500 kPa, for example from 100 kPa to 250 kPa.

In preferred embodiments, the reactants in a preceding transesterification are contacted in the liquid phase. Optionally, solvents may be used for diluting the reaction mixture, provided they do not negatively impact the transesterification reaction. Suitable solvents include aprotic, hydrocarbon solvents such as pentane, heptane and/or toluene.

Where a bed of solid acid catalyst, i.e. an acidic ion-exchange resin, is employed in connection with a preceding transesterification reaction, the flow rate of reactants, in terms of Liquid Hourly Space Velocity (LHSV) (volume of liquid feed stream/total volume of transesterification catalyst/hour), at which a pre-mixed alcohol/trihydrocarbyl orthoester reactant stream is contacted with the acidic ion-exchange resin catalyst is suitably in the range of from 0.1 to 50 $h^{-1}$.

Following completion of a preceding transesterification reaction, the transesterified orthoester may be isolated from the reaction mixture by known separation processes including filtration, chromatography (e.g. flash column chromatography) and/or distillation (e.g. vacuum distillation).

In accordance with the present invention, the trihydrocarbyl orthoester starting material is selectively converted to either the corresponding acetal or corresponding ether by means of hydrogenolysis. Advantageously, by selecting an appropriate temperature under which the hydrogenolysis is performed, the extent of hydrogenolysis/dealcoholation may be controlled so as to favour formation of the acetal or ether, as desired.

Where it is intended to favour the formation of the acetal (i.e. where it is favoured to limit the extent of the hydrogenolysis/dealcoholation) the hydrogenolysis may be operated at a temperature of 125° C. or less in order to maximize the selectivity for the acetal. Preferably, the hydrogenolysis step of the acetlization is performed at a temperature of 15° C. to 120° C., preferably from 20° C. to 110° C., more preferably from 40° C. to 105° C., most preferably from 60° C. to 100° C.

In some embodiments, following formation of the acetal, the process further comprises the subsequent step of:
  ii) subjecting the acetal to hydrogenolysis in the presence of a hydrogenation catalyst to form an ether;
wherein hydrogenolysis is performed at a temperature of 140° C. or greater, preferably at a temperature from 140° C. to 350° C., more preferably from 150° C. to 300° C., yet more preferably from 160° C. to 270° C., and most preferably from 175° C. to 250° C. Thus, in this embodiment the protected acetal compound may be first formed and for instance, transported and stored, before subsequent conversion to the ether. As will be appreciated, conversion to the ether can be conducted in a separate reactor in a different location to the initial hydrogenolysis to produce the acetal.

Similarly, in further embodiments, where an acetal compound is obtained by means of the process of the present invention, a further step of the process may include a converting the acetal obtained from the process into an aldehyde by acid catalyzed hydrolysis (i.e. performing a deprotection).

Where it is intended to favour the formation of the ether product (i.e. where it is favoured to maximise the extent of the hydrogenolysis/dealcoholation) the hydrogenolysis may be operated at a temperature of 140° C. or greater in order to maximize the selectivity for the ether. In preferred embodiments, the hydrogenolysis step of the etherification is performed at a temperature from 140° C. to 350° C., more preferably from 150° C. to 300° C., yet more preferably from 160° C. to 270° C., and most preferably from 175° C. to 250° C.

The hydrogenolysis/hydrogenation reaction may be performed at any suitable pressures at which the products are formed at an acceptable reaction rate, without risk of decomposition or substantial by-product formation that would otherwise negatively impact upon the advantages of the invention. Hydrogenolysis is, for example, suitably carried out at pressures of from 1,500 kPa absolute to 30,000 kPa absolute, preferably from 5,000 kPa absolute to 15,000 kPa absolute, more preferably from 7,500 kPa absolute to 12,500 kPa absolute. The molar ratio of the trihydrocarbyl orthoester to hydrogen can be from about 1:2 to about 1:100, and is preferably from about 1:4 to about 1:50.

Where a bed of hydrogenation catalyst is employed in connection with the hydrogenolysis reaction, the flow rate of a trihydrocarbyl orthoester feed stream, in terms of Liquid Hourly Space Velocity (LHSV) (volume of feed stream/total volume of hydrogenation catalyst/hour), over the catalyst bed, is suitably in the range of from 5 to 1,000 $h^{-1}$, preferably from 10 to 500 $h^{-1}$, more preferably from 20 to 200 $h^{-1}$, most preferably from 25 to 100 $h^{-1}$.

It has been found by the inventors that adjusting the time over which the trihydrocarbyl orthoester feed is in contact with the hydrogenation catalyst under hydrogenolysis conditions can also be used to manipulate the product distribution. In particular, increasing the contact time of reactants with the hydrogenation catalyst has been found to increase the extent of dealcoholation achievable at a particular reaction temperature. This is of particular benefit for increasing the proportion of ether that is formed in the etherification process of the invention. Thus, although the product distribution is primarily determined by the temperature at which hydrogeneolysis is conducted, the contact time of the trihydrocarbyl orthoester feed with the hydrogenation catalyst under hydrogenolysis conditions can be increased to enhance conversion and selectivity toward production of the ether when the reaction is conducted under the etherification temperatures described hereinbefore.

In preferred embodiments, where a bed of hydrogenation catalyst is employed in connection with the hydrogenolysis reaction as part of the etherification process described hereinbefore, the flow rate of a trihydrocarbyl orthoester feed stream, in terms of Liquid Hourly Space Velocity (LHSV) (volume of feed stream/total volume of hydrogenation catalyst/hour), is less than 60 $h^{-1}$. More preferably, the LHSV of the trihydrocarbyl orthoester feed stream is from 0.1 to 50 $h^{-1}$, more preferably from 1.0 $h^{-1}$ to 40 $h^{-1}$, most preferably from 5.0 to 35.0 $h^{-1}$.

In some embodiments, the hydrogenation catalyst useful in the hydrogenolysis reaction comprises a metal selected from nickel, palladium, platinum, rhodium, ruthenium, cobalt, copper and combinations thereof. Preferably, the catalyst comprises palladium. The catalyst may be supported with a support material selected from carbon, silica, alumina, silica-alumina, and aluminosilicate, preferably carbon. The carbon, where used, can be any one of the many forms of carbon e.g. graphite or activated carbon.

The catalytic metal may be deposited or impregnated on the support using conventional mixing or precipitation techniques. The catalyst composition suitably has a catalytic metal content of about 0.05% w/w to about 80% w/w. Within this range, when a relatively less active metal, such as nickel, is used as the catalytic metal, it is suitably used towards the higher end of this range, whereas when a relatively more active metal such as palladium is used as the catalytic metal, it is preferably used at the lower end of this range. The skilled person is able to select a suitable metal loading depending on the particular catalytic metal used. Thus, for instance, the preferred range for the less active catalytic metals is suitably from about 20% w/w to about 80% w/w, whereas for the more active catalytic metals, such as palladium, the preferred range is from about 0.05% w/w to about 20% w/w. These weight ranges are based solely on the weight of the catalytic metal and the support and does not take into account any water or moisture content associated with either component.

The hydrogenolysis reaction may optionally be carried out in the presence of a solvent. Examples of such solvents include aprotic, hydrocarbon solvents such as pentane, heptane and/or toluene. A sufficient amount of solvent can be used to dilute the trihydrocarbyl orthoester reactant to the desired concentration to facilitate handling and/or to maintain the reaction mass in solution.

The hydrogenolysis of the trihydrocarbyl orthoester with hydrogen in the presence of a catalyst composition as described above can be carried out in a slurry reactor, a fixed bed reactor, a spouted bed reactor or any other suitable reactor configuration such as, for example, a moving bed reactor. The trihydrocarbyl orthoester reactant may be in a gaseous phase and/or a liquid phase. The reaction can be carried out in a continuous, semi-continuous or a batch-type mode. The average residence time of the trihydrocarbyl orthoester reactant in contact with the catalyst composition during the formation of the corresponding saturated ether compound is suitably from about 5 minutes to about 30 hours, preferably from about 15 minutes to about 10 hours. As the skilled person is aware, a convenient way of modifying the residence time of the reactant in the hydrogeneolysis reaction is, for instance, to adjust the flow rate of an trihydrocarbyl orthoester reactant stream over a bed of the hydrogenation catalyst, as described hereinbefore.

The desired acetal or ether product may be isolated from the reaction mixture, in particular the alcohol by-product of the hydrogenolysis reaction, by known separation processes including filtration, chromatography (e.g. flash column chromatography) and/or distillation (e.g. vacuum distillation), filtration and distillation being favoured on an industrial scale.

A particular benefit of the present invention is that modifying the temperature of the hydrogenolysis reaction allows for convenient control over the product distribution in the preparation of acetals and ethers. The process is broadly applicable and a large variety of structural variation can be accommodated into the trihydrocarbyl orthoester starting material which can be carried forward into the acetal and ether products without the release of corrosive halogenated or sulfonate ester intermediates that have been associated with prior art etherification processes. The process of the present invention therefore represents a valuable route for the synthetic chemist to prepare valuable acetal and ether precursors and end products.

Particularly preferred ether end products that may be prepared by means of the present invention include ether base stocks for lubricant compositions. Thus, in some embodiments, the process of the present invention may further include the step of blending the ether product obtained from the process into a lubricant composition. The process of the present invention therefore also represents a means of preparing an ether which is useful as a component of a lubricating composition which avoids the formation of corrosive intermediates and which may be isolated from the reaction mixture more readily. By operating an etherification process in accordance with the present invention, it is possible to provide good conversion of the starting material to the ether product, and with high selectivity.

In accordance with another embodiment, the process of the invention also further comprises blending the ether obtained from the process into a lubricant composition by blending the ether with one or more additional base stocks and/or one or more lubricant additives. The ether obtained from the process of the invention may be miscible with conventional base stocks, including hydrocarbon base stocks, as well as with conventional lubricant additives. Moreover, such ether compounds may be used in a lubricant composition for example, in an amount of greater than about 1% by weight, such as greater than about 5% by weight, greater than about 10% by weight, greater than about 20% by weight or greater than about 30% by weight.

Base stocks other than the ether compound formed in the process of the present invention which are suitable for use blending for preparing a lubricant composition include non-aqueous base stocks, such as Group I, Group II, Group III, Group IV and Group V base stocks.

The lubricant composition may comprise a single lubricant additive, though it will typically comprise a combination of lubricant additives. The lubricant additives will typically be present in the lubricant composition in an amount of from about 5% to about 40% by weight, such as about 10% to about 30% by weight.

Suitable lubricant additives include detergents (including metallic and non-metallic detergents), friction modifiers, dispersants (including metallic and non-metallic dispersants), viscosity modifiers, dispersant viscosity modifiers, viscosity index improvers, pour point depressants, anti-wear additives, rust inhibitors, corrosion inhibitors, antioxidants (sometimes also called oxidation inhibitors), anti-foams (sometimes also called anti-foaming agents), seal swell agents (sometimes also called seal compatibility agents), extreme pressure additives (including metallic, non-metallic, phosphorus containing, non-phosphorus containing, sulphur containing and non-sulphur containing extreme pressure additives), surfactants, demulsifiers, anti-seizure agents, wax modifiers, lubricity agents, anti-staining agents, chromophoric agents, metal deactivators, and mixtures of two or more thereof.

In some embodiments, the lubricant composition comprises a detergent. Examples of detergents include ashless detergents (that is, non-metal containing detergents) and metal-containing detergents. Suitable non-metallic detergents are described for example in U.S. Pat. No. 7,622,431. Metal-containing detergents comprise at least one metal salt of at least one organic acid, which is called soap or surfactant. Suitable organic acids include for example, sulphonic acids, phenols (suitably sulphurised and including for example, phenols with more than one hydroxyl group, phenols with fused aromatic rings, phenols which have been modified for example, alkylene bridged phenols, and Mannich base-condensed phenols and saligenin-type phenols, produced for example by reaction of phenol and an aldehyde under basic conditions) and sulphurised derivatives thereof, and carboxylic acids including for example, aromatic carboxylic acids (for example hydrocarbyl-substituted salicylic acids and derivatives thereof, for example hydrocarbyl substituted salicylic acids and sulphurised derivatives thereof).

In some embodiments, the lubricant composition comprises a friction modifier. Suitable friction modifiers include for example, ash-producing additives and ashless additives. Examples of suitable friction modifiers include fatty acid derivatives including for example, fatty acid esters, amides, amines, and ethoxylated amines. Examples of suitable ester friction modifiers include esters of glycerol for example, mono-, di-, and tri-oleates, mono-palmitates and mono-myristates. A particularly suitable fatty acid ester friction modifier is glycerol monooleate. Examples of suitable friction modifiers also include molybdenum compounds for example, organo molybdenum compounds, molybdenum dialkyldithiocarbamates, molybdenum dialkylthiophosphates, molybdenum disulphide, tri-molybdenum cluster dialkyldithiocarbamates, non-sulphur molybdenum compounds and the like. Suitable molybdenum-containing compounds are described for example, in EP 1533362 A1 for example in paragraphs [0101] to [0117].

In some embodiments, the lubricant composition comprises a dispersant. Examples of suitable ashless dispersants include oil soluble salts, esters, amino-esters, amides, imides and oxazolines of long chain hydrocarbon-substituted mono- and polycarboxylic acids or anhydrides thereof thiocarboxylate derivatives of long chain hydrocarbons; long chain aliphatic hydrocarbons containing polyamine moieties attached directly thereto; Mannich condensation products formed by condensing a long chain substituted phenol with formaldehyde and polyalkylene polyamine; Koch reaction products and the like.

In some embodiments, the lubricant composition comprises a dispersant viscosity modifier. Examples of suitable dispersant viscosity modifiers and methods of making them are described in WO 1999/021902, WO 2003/099890 and WO 2006/099250.

In some embodiments, the lubricant composition comprises a viscosity index improver. Examples of suitable viscosity modifiers include high molecular weight hydrocarbon polymers (for example polyisobutylene, copolymers of ethylene and propylene and higher alpha-olefins); polyesters (for example polymethacrylates); hydrogenated poly (styrene-co-butadiene or isoprene) polymers and modifications (for example star polymers); and esterified poly (styrene-co-maleic anhydride) polymers. Oil-soluble viscosity modifying polymers generally exhibit number average molecular weights of at least about 15000 to about 1000000, such as about 20000 to about 600000 as determined by gel permeation chromatography or light scattering methods.

In some embodiments, the lubricant composition comprises a pour point depressant. Examples of suitable pour point depressants include $C_8$ to $C_{18}$ dialkyl fumarate/vinyl acetate copolymers, methacrylates, polyacrylates, polyarylamides, polymethacrylates, polyalkyl methacrylates, vinyl fumarates, styrene esters, condensation products of haloparaffin waxes and aromatic compounds, vinyl carboxylate polymers, terpolymers of dialkyfumarates, vinyl esters of fatty acids and allyl vinyl ethers, wax naphthalene and the like. In at least some examples, the at least one lubricant additive includes at least one anti-wear additive. Examples of suitable anti-wear additives include non-phosphorus containing additives for example, sulphurised olefins. Examples of suitable anti-wear additives also include phosphorus-containing anti-wear additives. Examples of suitable ashless phosphorus-containing anti-wear additives include trilauryl phosphite and triphenylphosphorothionate and those disclosed in paragraph [0036] of US 2005/0198894. Examples of suitable ash-forming, phosphorus-containing anti-wear additives include dihydrocarbyl dithiophosphate metal salts. Examples of suitable metals of the dihydrocarbyl dithiophosphate metal salts include alkali and alkaline earth metals, aluminium, lead, tin, molybdenum, manganese, nickel, copper and zinc. Particularly suitable dihydrocarbyl dithiophosphate metal salts are zinc dihydrocarbyl dithiophosphates (ZDDP).

In some embodiments, the lubricant composition comprises a rust inhibitor. Examples of suitable rust inhibitors include non-ionic polyoxyalkylene polyols and esters thereof, polyoxyalkylene phenols, polyoxyalkylene polyols, anionic alky sulphonic acids, zinc dithiophosphates, metal phenolates, basic metal sulphonates, fatty acids and amines.

In some embodiments, the lubricant composition comprises a corrosion inhibitor. Examples of suitable corrosion inhibitors include phosphosulphurised hydrocarbons and the products obtained by the reaction of phosphosulphurised hydrocarbon with an alkaline earth metal oxide or hydroxide, non-ionic polyoxyalkylene polyols and esters thereof, polyoxyalkylene phenols, thiadiazoles, triazoles and anionic alkyl sulphonic acids. Examples of suitable epoxidised ester corrosion inhibitors are described in US 2006/0090393.

In some embodiments, the lubricant composition comprises an antioxidant. Examples of suitable antioxidants include alkylated diphenylamines, N-alkylated phenylenediamines, phenyl-a-naphthylamine, alkylated phenyl-a-naphthylamines, dimethylquinolines, trimethyldihydroquinolines and oligomeric compositions derived therefrom, hindered phenolics (including ashless (metal-free) phenolic compounds and neutral and basic metal salts of certain phenolic compounds), aromatic amines (including alkylated and non-alkylated aromatic amines), sulphurised alkyl phenols and alkali and alkaline earth metal salts thereof, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds (for example, copper dihydrocarbyl thio- or thio-phosphate, copper salts of a synthetic or natural carboxylic acids, for example a $C_8$ to $C_{18}$ fatty acid, an unsaturated acid or a branched carboxylic acid, for example basic, neutral or acidic Cu(I) and/or Cu(II) salts derived from alkenyl succinic acids or anhydrides), alkaline earth metal salts of alkylphenolthioesters, suitably containing $C_5$ to $C_{12}$ alkyl side chains, calcium nonylphenol sulphide, barium t-octylphenyl sulphide, dioctylphenylamine, phosphosulphised or sulphurised hydrocarbons, oil soluble phenates, oil soluble sulphurised phenates, calcium dodecylphenol sulphide, phosphosulphurised hydrocarbons, sulphurised hydrocarbons, phosphorus esters, low sulphur peroxide decomposers and the like.

In some embodiments, the lubricant composition comprises an antifoam agent. Examples of suitable anti-foam agents include silicones, organic polymers, siloxanes (including poly siloxanes and (poly) dimethyl siloxanes, phenyl methyl siloxanes), acrylates and the like.

In some embodiments, the lubricant composition comprises a seal swell agent. Examples of suitable seal swell agents include long chain organic acids, organic phosphates, aromatic esters, aromatic hydrocarbons, esters (for example butylbenzyl phthalate) and polybutenyl succinic anhydride.

The lubricant composition may comprise lubricant additives in the amounts shown in Table 1.

TABLE 1

| Additive type | Lubricant composition | |
|---|---|---|
| | Suitable amount (actives) if present by weight | Preferred amount (actives) if present by weight |
| Phosphorus-containing anti-wear additives | Corresponding to about 10 to about 6000 ppm P | Corresponding to about 10 to about 1000 ppm P |
| Molybdenum-containing anti-wear additives | Corresponding to about 10 to about 1000 ppm Mo | Corresponding to about 40 to about 600 ppm Mo |
| Boron-containing anti-wear additives | Corresponding to about 10 to about 500 ppm B | Corresponding to about 50 to about 100 ppm B |
| Friction modifiers | About 0.01 to about 5% | About 0.01 to about 1.5% |
| Molybdenum-containing friction modifiers | Corresponding to about 10 to about 1000 ppm Mo | Corresponding to about 400 to about 850 ppm Mo |
| Dispersants | About 0.1 to about 20% | About 0.1 to about 8% |
| Detergents | About 0.01 to about 6% | About 0.01 to about 4% |
| Viscosity index improvers | About 0.01 to about 20% | About 0.01 to about 15% |
| Pour point depressants | About 0.01 to about 5% | About 0.01 to about 1.5% |
| Corrosion and/or rust inhibitors | About 0.01 to about 5% | About 0.01 to about 1.5% |
| Anti-oxidants | About 0.01 to about 10% | About 0.5 to 5 about % |
| Antifoams containing silicon | Corresponding to about 1 to about 20 ppm Si | Corresponding to about 1 to about 10 ppm Si |

The lubricant compositions preparable in accordance with the present invention may have a kinematic viscosity at 40° C. of less than about 60 cSt, such as less than about 55 cSt, or less than about 50 cSt. The lubricant compositions may have a kinematic viscosity at 100° C. of less than about 12 cSt, such as less than about 10 cSt, or less than about 9.5 cSt. The lubricant compositions may have a viscosity index of greater than about 100, such as greater than about 110, or greater than about 120. The kinematic viscosity at 40° C. and the kinematic viscosity at 100° C. may be measured according to ASTM D445. The viscosity index may be calculated according to ASTM D2270.

The lubricant compositions may have a Noack volatility of less than about 25%, such as less than about 15%, or less than about 10% by weight. Noack volatility may be measured according to CEC-L-40-A-93.

The lubricant compositions may have a viscosity at 150° C. and a shear rate of $10^6$ s$^{-1}$ of no greater than 3 cP, such as no greater than 2.8 cP. This high temperature high shear viscosity may be measured according to CEC-L-36-A-90.

The lubricant compositions may have at least one of:

an oxidative stability performance on a CEC-L-088-02 test indicated by an absolute viscosity increase at 40° C. of no more than 45 cSt, such as no more than 35 cSt or no more than 25 cSt; a fuel economy performance on a CEC-L-054-96 test of at least 2.5%, such as at least 3%; and a piston cleanliness performance on a CEC-L-088-02 test indicated by an overall piston merit of at least 8.5, such as 9.

The lubricant compositions may have a cold-crankcase simulator performance at −30° C. of less than about 3000, such as less than about 2800, or less than about 2750, for example as measured according to ASTM D5293.

Preferred lubricant compositions meet the requirements set out in SAE J300.

In a yet further embodiment of the invention, after the lubricant composition has been prepared, the process may further comprise lubricating a surface with the lubricant composition by supplying the lubricant composition to a surface for lubrication.

Suitable surfaces include those in power transmission systems for example drive lines and gear boxes for example for vehicles including for example passenger vehicles and heavy duty vehicles; and those in internal combustion engines, for example the crankcases of internal combustion engines. Suitable surfaces also include those in turbine bearings for example in water turbine bearings.

Suitable internal combustion engines include, for example, engines used in automotive applications, engines used in marine applications and engines used in land-based power generation plants. The lubricant compositions are particularly suited to use in an automotive internal combustion engine.

The invention will now be described with reference to the accompanying examples, which are not limiting in nature.

EXAMPLES

Example 1—Selective Acetal Formation from Orthoesters

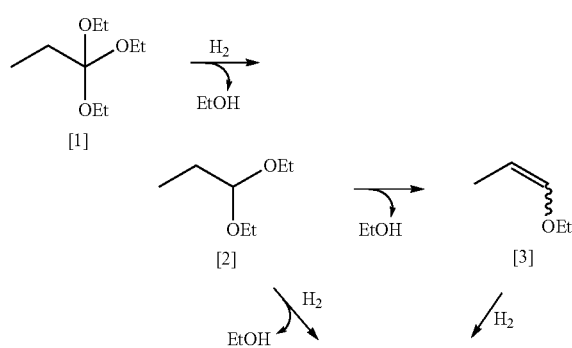

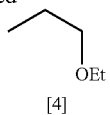

A solution of 1,1,1-triethoxypropane [1] (17.6 g, 100 mmol) in heptane (200 mL) was passed over a bed of palladium on charcoal catalyst (10 wt. % loading of palladium) (0.880 mL) at a flow rate of 1 mL/min (LHSV of 68 h$^{-1}$), pressure of 90 bar$_g$ and over a range of temperatures up to 125° C. (20, 50, 75, 100, and 125° C.). The reactions took place in the liquid phase. Products of each of the reactions were analysed by gas chromatography (GC) and results are provided in Table 2 below.

TABLE 2

| Experiment | Temperature (° C.) | Hydrogen flow rate (mL/min) | EtOH (mol %) | Ether [4] (mol %) | E/Z vinyl ether [3] (mol %) | Acetal [2] (mol %) | Orthoester [1] (mol %) |
|---|---|---|---|---|---|---|---|
| Comp. A | 20 | 0 | 0.00 | 0.00 | 0.02 | 0.00 | 99.98 |
| A | 20 | 60 | 37.4 | 0.02 | 0.16 | 43.9 | 18.5 |
| B | 50 | 60 | 48.2 | 0.49 | 1.98 | 49.3 | 0.00 |
| C | 75 | 60 | 49.0 | 0.55 | 0.82 | 49.7 | 0.00 |
| D | 100 | 60 | 47.6 | 0.09 | 0.66 | 51.7 | 0.00 |
| E | 125 | 60 | 48.5 | 2.68 | 0.88 | 47.9 | 0.00 |

The yield of the acetal [2] (1,1-diethoxypropane) from the orthopropionate [1] (1,1,1-triethoxypropane) was significant over the temperatures tested in Experiments A to E (20° C. up to 125° C.), with the greatest yield observed at a temperature of 100° C. (Experiment D). Very little conversion to the ether [4] (1-ethoxypropane) was observed over this temperature range. Comparative yields for the ether [4] and the acetal [2] are provided in Table 3 below which demonstrate that it is possible to control the extent of dealcoholation of the orthoester so as to favour formation of the acetal over the ether.

TABLE 3

| Experiment | Temperature (° C.) | Hydrogen flow rate (mL/min) | Ether [4] yield (%) | Acetal [2] yield (%) |
|---|---|---|---|---|
| Comp. A | 20 | 0 | 0.00 | 0.00 |
| A | 20 | 60 | 0.02 | 70.2 |
| B | 50 | 60 | 0.95 | 95.2 |
| C | 75 | 60 | 1.08 | 97.3 |
| D | 100 | 60 | 0.17 | 98.6 |
| E | 125 | 60 | 5.20 | 93.1 |

Example 2—Selective Ether Formation from Orthoesters

The hydrogenolysis reaction was performed as described in Example 1 but operated at a temperature of 150° C. Products of the reaction were analysed by gas chromatography (GC) and results are provided in Table 4 below.

TABLE 4

| Experiment | Temperature (° C.) | Hydrogen flow rate (mL/min) | EtOH (mol %) | Ether [4] (mol %) | E/Z vinyl ether [3] (mol %) | Acetal [2] (mol %) | Orthoester [1] (mol %) |
|---|---|---|---|---|---|---|---|
| F | 150 | 60 | 62.8 | 13.7 | 0.04 | 23.4 | 0.00 |

The yield of the ether [4] (1-ethoxypropane) from the orthopropionate [1] (1,1,1-triethoxypropane) increased as the temperature of the reaction increased above 100° C., with reduced quantities of the acetal [2] (1,1-diethoxypropane) in the resulting product. Comparative yields for the ether [4] and the acetal [2] are provided in Table 5 below which demonstrates that it is possible to control the extent of dealcoholation of the orthoester so as to favour formation of the ether. Increasing the temperature of the dehydrongenolysis reaction further is capable of affording the ether as the major product of the reaction.

TABLE 5

| Experiment | Temperature (° C.) | Hydrogen flow rate (mL/min) | Ether [4] yield (%) | Acetal [2] yield (%) |
|---|---|---|---|---|
| F | 150 | 60 | 36.9 | 63.0 |

Example 3—Selective Ether Formation from Orthoesters and Effect of Residence Time The hydrogenolysis reaction was performed as described in Example 1 but operated at a temperature of 150° C. and at half the feed flow rate (0.5 mL/min—LHSV of 34 h$^{-1}$), leading to a higher residence time of the feed in the hydrogenolysis reaction. Products of the reaction were analysed by gas chromatography (GC) and results are provided in Table 6 below.

TABLE 6

| Experiment | Temperature (° C.) | Hydrogen flow rate (mL/min) | EtOH (mol %) | Ether [4] (mol %) | E/Z vinyl ether [3] (mol %) | Acetal [2] (mol %) | Orthoester [1] (mol %) |
|---|---|---|---|---|---|---|---|
| G | 150 | 60 | 55.9 | 23.7 | 0.00 | 20.4 | 0.00 |

The yield of the ether [4] (1-ethoxypropane) from the orthopropionate [1] (1,1,1-triethoxypropane) was significantly increased by reducing the feed flow rate (LHSV) so as to increase the residence time of the reactant. Comparative yields for the ether [4] and the acetal [2] are provided for Experiment F, having a flow rate in terms of LHSV of 68 h$^{-1}$, and Experiment G having a lower flow rate in terms LHSV of 34 h$^{-1}$, are provided in Table 7 below. These results demonstrate that it is possible to enhance dealcoholation of the orthoester so as to favour formation of the ether yet further by increasing reactant residence time to provide the ether as the major product.

TABLE 7

| Experiment | Temperature (° C.) | Hydrogen flow rate (mL/min) | LHSV (h$^{-1}$) | Ether [4] yield (%) | Acetal [2] yield (%) |
|---|---|---|---|---|---|
| F | 150 | 60 | 68 | 36.9 | 63.0 |
| G | 150 | 60 | 34 | 53.8 | 46.2 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A process for preparing an acetal, said process comprising the step of:
   i) subjecting a trihydrocarbyl orthoester to hydrogenolysis in the presence of a hydrogenation catalyst to form an acetal;
   wherein hydrogenolysis is performed at a temperature of 125° C. or less.

2. The process of claim 1, wherein said hydrogenolysis is performed at a temperature of 15° C. to 120° C.

3. The process of claim 1, wherein the trihydrocarbyl orthoester is of formula (I):

(I)

wherein: $R_1$ is selected from H and aliphatic hydrocarbyl; and $R_2$ is aliphatic hydrocarbyl.

4. The process of claim 3, wherein $R_1$ is selected from H, $C_1$-$C_{40}$ alkyl, $C_3$-$C_{40}$ cycloalkyl and $C_4$-$C_{40}$ cycloalkyl-substituted-alkyl and $R_2$ is selected from $C_1$-$C_{40}$ alkyl, $C_3$-$C_{40}$ cycloalkyl and $C_4$-$C_{40}$ cycloalkyl-substituted-alkyl.

5. The process of claim 1, wherein the hydrogenolysis is performed with the trihydrocarbyl orthoester in a liquid phase.

6. The process of claim 1, further comprising the preceding step of preparing a trihydrocarbyl orthoester of formula (I) where $R_2$ is $C_4$-$C_{40}$ alkyl, $C_3$-$C_{40}$ cycloalkyl and $C_4$-$C_{40}$ cycloalkyl-substituted-alkyl, said preceding step comprising reacting a trimethyl orthoester and/or triethyl orthoester with a molar excess of an alcohol of formula $R_2OH$ in the presence of an acidic catalyst, where $R_2$ is $C_4$-$C_{40}$ alkyl, $C_3$-$C_{40}$ cycloalkyl and $C_4$-$C_{40}$ cycloalkyl-substituted-alkyl.

7. The process of claim 6, wherein the alcohol and orthoester are contacted in a molar ratio of at least 5:1.

8. The process of claim 6, wherein the acidic catalyst is selected from sulfuric acid, p-toluenesulfonic acid, benzenesulfonic acid, hydrochloric acid, phosphoric acid and an acidic ion-exchange resin.

9. The process of claim 8, wherein the acidic ion-exchange resin is an acidic macroreticular-type ion-exchange resin or an acidic gel-type ion-exchange resin.

10. The process of claim 9, wherein the hydrogenation catalyst comprises a metal selected from nickel, palladium, platinum, rhodium, ruthenium, cobalt, copper and combinations thereof.

11. The process of claim 1, wherein the hydrogenolysis is conducted at a pressure of from 1,500 kPa absolute to 30,000 kPa absolute.

12. The process of claim 1, further comprising converting the acetal obtained from the process into an aldehyde by acid catalyzed hydrolysis.

13. The process of claim 1, further comprising the step of:
   ii) subjecting the acetal to hydrogenolysis in the presence of a hydrogenation catalyst to form an ether;
   wherein hydrogenolysis is performed at a temperature of 140° C. or greater.

14. The process of claim 13, wherein said hydrogenolysis is performed at a temperature of 140° C. to 350° C.

15. A process for preparing an ether, said process comprising the step of:
   i) subjecting a trihydrocarbyl orthoester to hydrogenolysis in the presence of a hydrogenation catalyst to form an ether;
   wherein hydrogenolysis is performed at a temperature of 140° C. or greater.

16. The process of claim 15, wherein said hydrogenolysis is performed at a temperature from 140° C. to 350° C.

17. The process of claim 15, wherein a bed of hydrogenation catalyst is contacted with a trihydrocarbyl orthoester feedstream.

18. The process of claim 17, wherein the flow rate of the trihydrocarbyl orthoester feed stream, in terms of Liquid Hourly Space Velocity (LHSV) (volume of feed stream/total volume of hydrogenation catalyst/hour), is less than 60 $h^{-1}$.

19. The process of claim 15, or any one of the preceding claims depending therefrom, further comprising blending the ether obtained from the process with one or more additional base stocks and/or one or more lubricant additives into a lubricant composition.

20. The process of claim 19, wherein the ether is present in the lubricant composition in an amount of greater than 1% by weight.

21. The process of claim 19, further comprising supplying the lubricant composition to a surface for lubrication, such as a surface in an internal combustion engine.

* * * * *